(12) United States Patent
Henke et al.

(10) Patent No.: US 12,410,875 B2
(45) Date of Patent: Sep. 9, 2025

(54) FLUID-TIGHT HOSE CONNECTION

(71) Applicant: OLYMPUS Winter & Ibe GmbH, Hamburg (DE)

(72) Inventors: Philipp Henke, Hamburg (DE); Nils Torkuhl, Barsbuettel (DE); Alrun Thuemen, Hamburg (DE)

(73) Assignee: OLYMPUS Winter & Ibe GmbH, Hamburg (DE)

( * ) Notice: Subject to any disclaimer, the term of this patent is extended or adjusted under 35 U.S.C. 154(b) by 135 days.

(21) Appl. No.: 17/684,563

(22) Filed: Mar. 2, 2022

(65) Prior Publication Data
US 2022/0282816 A1 Sep. 8, 2022

(30) Foreign Application Priority Data
Mar. 2, 2021 (DE) .................... 10 2021 105 016.2

(51) Int. Cl.
 *A61B 1/00* (2006.01)
 *F16L 33/18* (2006.01)
 *F16L 33/22* (2006.01)

(52) U.S. Cl.
 CPC ........ *F16L 33/222* (2013.01); *A61B 1/00128* (2013.01); *F16L 33/18* (2013.01); *F16L 33/223* (2013.01)

(58) Field of Classification Search
 CPC . A61B 1/00128; A61B 1/012; A61B 1/00112; A61B 1/00119; A61B 25/005; F16L 21/007; F16L 11/086; F16L 33/22; F16L 33/222
 See application file for complete search history.

(56) References Cited

U.S. PATENT DOCUMENTS

| | | | | |
|---|---|---|---|---|
| 2,878,039 A | * | 3/1959 | Hoegee | F16L 33/222 285/354 |
| 4,229,029 A | * | 10/1980 | Boyer | F16L 33/222 285/323 |
| 4,967,732 A | * | 11/1990 | Inoue | A61B 1/00137 600/149 |
| 4,968,732 A | | 11/1990 | Burba et al. | |
| 5,090,741 A | * | 2/1992 | Yokomatsu | F16L 33/16 285/101 |
| 5,275,152 A | * | 1/1994 | Krauter | A61B 1/0052 600/129 |
| 5,735,793 A | * | 4/1998 | Takahashi | A61B 1/00128 600/153 |

FOREIGN PATENT DOCUMENTS

JP  05-020706 U  *  3/1993  ............... A61B 1/00

* cited by examiner

*Primary Examiner* — Anh Tuan T Nguyen
*Assistant Examiner* — Rynae E Boler
(74) *Attorney, Agent, or Firm* — Scully, Scott, Murphy & Presser, P.C.

(57) ABSTRACT

A fluid-tight hose connection for a surgical instrument including: a hose having an inner hose and an outer protective hose surrounding the inner hose, wherein the inner hose has a coiled hose portion at an end portion of the hose; and a sleeve having a wedge-shape in a longitudinal section, the sleeve being arranged between the coiled hose portion of the inner hose and the outer protective hose.

17 Claims, 3 Drawing Sheets

FLUID-TIGHT HOSE CONNECTION

CROSS-REFERENCE TO RELATED APPLICATION

The present application is based upon and claims the benefit of priority from DE 10 2021 105 016.2 filed on Mar. 2, 2021, the entire contents of which is incorporated herein by reference.

BACKGROUND

Field

The present disclosure relates generally to a surgical instrument, such as an endoscope, and more particularly to a fluid-tight hose connection for a surgical instrument, such as an endoscope, and to a surgical system comprising the surgical instrument, such as an endoscope. Moreover, the present disclosure relates to a use of a hose connection.

Prior Art

It is known that endoscopes are used as surgical instruments to perform examinations in cavities or hollow organs of patients. For this purpose, the endoscopes have a long, flexible, hose-like shaft, which can be inserted, for example, into an opening in the body of a patient. Inside this hose, multiple cables, light bundles, working channels, etc. are received for this purpose. To connect the hose to additional units, corresponding couplings are provided at the end of a hose. The hose connections here must be configured to be fluid-tight.

An object is to provide a fluid-tight hose connection for surgical instruments, such as without inlet-side narrow points in the region of the coupling, wherein the hose connection can be mountable without adhesive and/or welding processes.

Such object can be solved by a fluid-tight hose connection for a surgical instrument, such as an endoscope, with a hose, wherein the hose has an inner hose which is round, such as circular, in cross-section and an outer protective hose surrounding the inner hose, wherein the inner hose has a coiled hose portion at one end portion of the hose, wherein a sleeve, which is wedge-shaped in the longitudinal section, is arranged between the coiled hose portion, which can be circular in cross-section, of the inner hose and the protective hose.

The inner hose can be provided with a coiled hose portion at a front-face end of the hose, wherein the coiled hose portion, which can be circular in cross-section, is surrounded at the end of the hose by a sleeve, which is configured to be wedge-shaped in the longitudinal section. By using a cone-shaped sleeve, the cross-section of the inner hose and of the coiled hose portion in the region of the end of the hose is maintained or respectively not narrowed along the longitudinal extension of the hose, wherein a fluid-tight hose connection is formed by the arrangement of the cone-shaped sleeve on the outside of the coiled hose portion and with a clamping or tensioning of the adjacent protective hose.

When forming or assembling the fluid-tight hose connection, no welding or adhering of the parts working together takes place. The components of the hose connection are fixed to each other by mechanical forces, such as tensioning forces or clamping forces. In addition, the hose connection can be easily assembled and disassembled.

Furthermore, the sleeve which can be wedge-shaped in longitudinal section can be configured as a sleeve body with a truncated-conical outer side facing the protective hose and with a cylindrical hollow space partially receiving the coiled hose portion of the inner hose.

In addition, the hose connection that the sleeve which can be wedge-shaped in longitudinal section, can be arranged between the coiled hose portion of the inner hose and the protective hose such that an end of the sleeve that is wider is diameter faces the free end of the hose.

In addition, a braided hose, such as a glass silk braided hose, surrounding the inner hose can be arranged between the coiled hose portion of the inner hose and the outer protective hose, wherein the braided hose can surround the sleeve which is wedge-shaped in the longitudinal section at the free end of the hose.

The inner hose can be formed from a flexible material, such as plastic or silicone, and can have, at the end, a coiled hose portion produced. The coiled hose portion can be formed from stainless steel. Here, the coiled hose portion can be configured as a stainless steel coil. The sleeve, which can be wedge-shaped in longitudinal section, or respectively the sleeve body can be produced from a plastic, such as PEEK (polyether ether ketone).

A secure arrangement of the protective hose on the hose end results from the sleeve which is wedge-shaped in the longitudinal section can have a peripheral groove in the circumferential direction for receiving the protective hose, such as for receiving the end of the protective hose and the end of the braided hose, wherein the groove in the sleeve which can be wedge-shaped in longitudinal section can face the end of the hose. The groove can enable the front-face end of the protective hose and the end of the braided hose to be received or positioned in the peripheral groove of the sleeve which is wedge-shaped in the longitudinal section.

A sealing body surrounding the protective hose can be arranged on the outside of the protective hose in the region of the sleeve which is wedge-shaped in the longitudinal section. As a result, the sealing takes place from the outside to the inside using the sealing body, which can be pressed against the outer protective hose by means of a corresponding tensioning device, thereby creating a surface pressure of the outer protective hose against the sleeve which is wedge-shaped in the longitudinal section.

The sealing body can have a truncated-conical interior for receiving the end portion of the hose, which end portion surrounds the sleeve, which is wedge-shaped in the longitudinal section.

The sealing body can be configured to be wedge-shaped in the longitudinal section, wherein the sealing body can have a truncated-conical hollow space receiving the end portion of the hose and a basically cylindrical outer circumferential face and/or the sealing body can have at least one peripheral rib, such as a sealing rib, on the outer circumferential face, and/or wherein the sealing body can have a peripheral, receiving groove on its outside in the circumferential direction for receiving a sealing body, such as a sealing ring. Here, the sealing body can be arranged on the protective hose as a type of counter-wedge to the sleeve, which is wedge-shaped in the longitudinal section. In one embodiment, the protective hose and, if applicable, the braided hose can be arranged or clamped between the sleeve which is wedge-shaped in the longitudinal section and the sealing body which can be configured to be wedge-shaped in a longitudinal section.

The sealing body which can be wedge-shaped in the longitudinal section can be arranged on the protective hose such that an end of the sealing body with a smaller diameter faces the end of the hose.

In addition, the coiled hose portion of the inner hose can have a coiled end portion, wherein the coiled end portion can be configured as an end-side, such as a crimped, protrusion, wherein the radial distance of the protrusion to a central longitudinal axis of the coiled hose portion can be larger than the radial distance of the coiled hose portion facing away from the coiled end portion to the central longitudinal axis of the coiled hose portion. In this case, the coiled end portion can be reshaped or crimped, for example, with a bending tool, wherein the coiled end portion can be configured to be spiral-shaped or partially spiral-shaped in relation to the coiled hose portion which can be surrounded by the protective hose. As a result, the inner passage or the diameter of the coiled hose portion or respectively of the coiled end portion is not tapered. For example, it is achieved by the crimped protrusion or respectively the crimped geometry of the coiled end portion that the coiled hose portion can be configured so that it cannot rotate or slip in relation to the sleeve.

Furthermore, the coiled end portion can be arranged, such as clamped, between the sleeve which is wedge-shaped in the longitudinal section and a coupling sleeve arranged at the front-face end of the hose, and/or that the coiled end portion can surround from the outside, such as by forming a clamping tension, a continuation body, which can extend to the front-face end of the hose and can be partially circular in cross-section, of the sleeve which can be wedge-shaped in cross-section. In this case, a coupling sleeve can be arranged at the front-face end of the hose, wherein the spiral-shaped or crimped coiled end portion can be arranged between the sleeve which is wedge-shaped in the longitudinal section and the coupling sleeve. As a result, the sleeve can be fixed to the coiled hose portion or respectively the coiled end portion. The sleeve which is wedge-shaped in the longitudinal section can also be secured against rotational slipping by the arrangement and the shape of the coiled end portion on the continuation body. Through the abutting contact of the coiled end portion against the outside of the continuation body of the sleeve, the sleeve can be fixed so that it cannot slip due to formation of a clamping tension.

The sleeve which is wedge-shaped in the longitudinal section can have a collar, such as with an undercut, facing the front-face end of the hose and running peripherally in the circumferential direction of the sleeve. Through the formation of a collar on the front-face end of the sleeve, which is wedge-shaped in the longitudinal section, the coupling sleeve on the front face of the hose can be securely connected to the sleeve which is wedge-shaped in the longitudinal section.

The collar of the sleeve which is wedge-shaped in the longitudinal section can have a latching contour for a latching projection of a front-face coupling sleeve. By arranging the latching projection of the front-face coupling sleeve in the latching contour of the sleeve, the front-face coupling sleeve can be arranged on the hose end so that it cannot slip. The coupling sleeve can be produced from a plastic such as polyvinylidene fluoride (PVDF), polyether ether ketone (PEEK), or polysulfones (PPSU). The front-face coupling sleeve can be arranged in this case at the end of the hose.

Furthermore, the end portion of the hose can be surrounded by an outer cuff, such as an outer nut, wherein the outer cuff can have an inner thread for an outer thread, which interacts with the inner thread, of a connector body, such as of a medical device or of a surgical instrument, which connector body can be introduced between the sealing body and the inner thread. The outer cuff here can surround the end portion of the hose in the region in which the sleeve which is wedge-shaped in the longitudinal section and the sealing body interacting with it are arranged. The outer protective hose and the braided hose can be arranged or respectively clamped between the sleeve which is wedge-shaped in the longitudinal section and the sealing body configured as a counter-wedge. Screwing the outer cuff or the outer nut with a connector body can press the sealing body against the outer protective hose, thereby forming a fluid-tight connection on the hose end. The hose connection can be assembled in this case without using welding methods, such as spot welding methods, or without adhesive methods. In addition, the hose connection can be easily disassembled.

Moreover, such object can be achieved with a surgical system or a surgical instrument, such as an endoscope, that is configured with a fluid-tight hose connection. We refer to the above explanations accordingly in order to avoid repetitions. In this case, light bundles or electrical supply cables or signal cables, for example, can be guided inside the inner hose.

Furthermore, such object can be achieved by a use of a fluid-tight hose connection described above in a surgical system or in a surgical instrument, such as an endoscope. In this regard, reference is expressly made to the above statements.

BRIEF DESCRIPTION OF THE DRAWINGS

Further features will become evident from the description of embodiments, together with the claims and the appended drawings. Embodiments can fulfill individual features or a combination of several features.

The embodiments are described below, without restricting the general idea of the invention, based on the exemplary embodiments in reference to the drawings, whereby we expressly refer to the drawings with regard to the disclosure of all details that are not explained in greater detail in the text. In the drawings.

In the drawings, the same or similar elements and/or parts are, in each case, provided with the same reference numerals such that they are not introduced again in each case.

DETAILED DESCRIPTION

Figure 1:
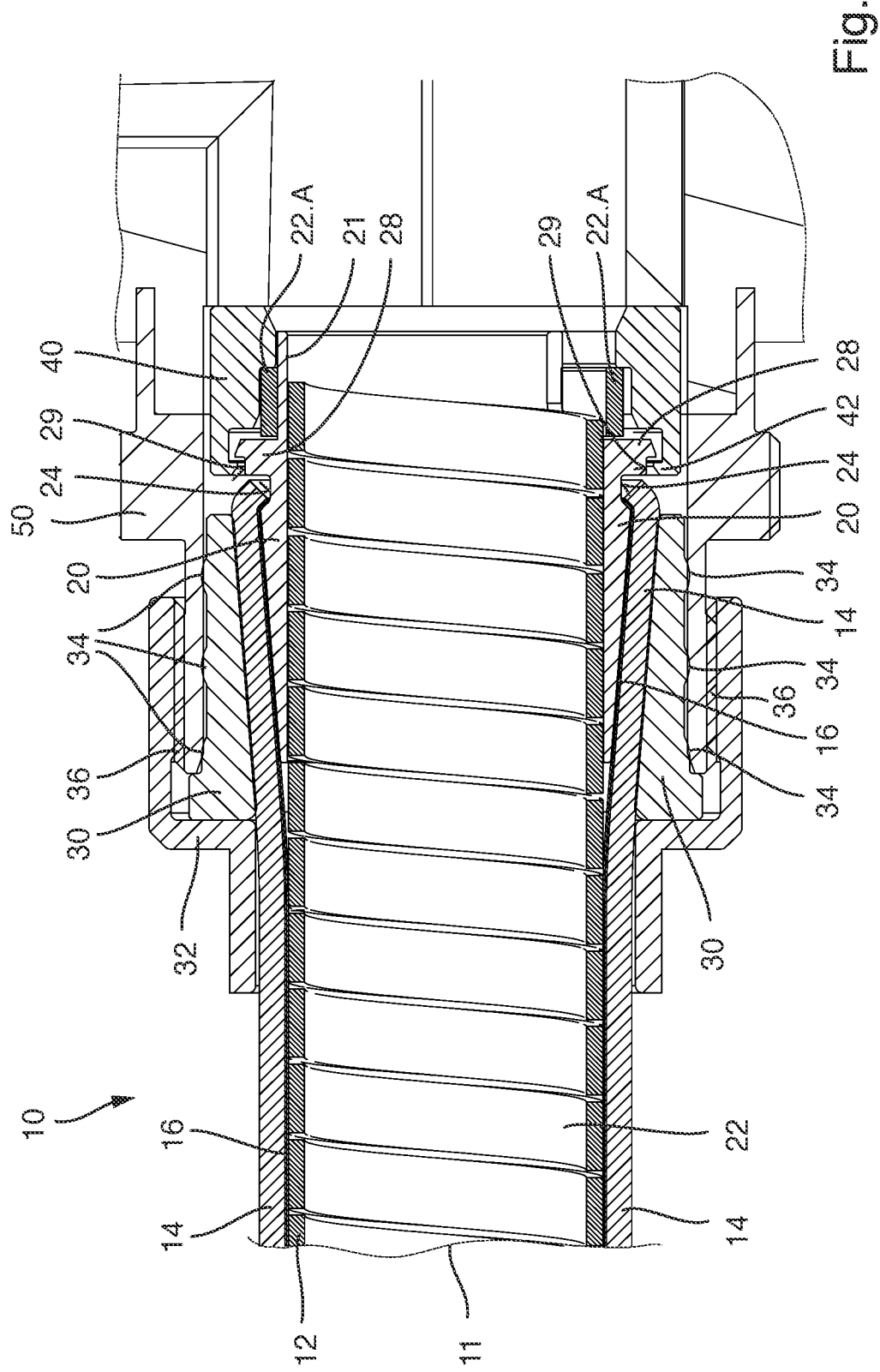
FIG. 1 schematically illustrates a cross-section through a hose connection.

FIG. 1 shows a longitudinal section of an exemplary embodiment of a fluid-tight hose connection 10. The hose connection 10 is in this case a component of a surgical instrument, such as an endoscope, or of a surgical system.

The hose connection 10 has a hose 11 extending longitudinally. The hose 11 has an inner hose 12 and a protective hose 14, wherein the inner hose 12 is surrounded by the outer protective hose 14. In the longitudinal extension of the hose 11, a braided hose 16, such as being made from glass silk, is arranged between the inner hose 12 and the protective hose 14. The braided hose 16 runs in the longitudinal extension between the outer protective hose 14 and the inner hose 12.

The protective hose 14 is produced, for example, from silicone. Furthermore, the braided hose 16 is manufactured from a glass silk mesh.

The inner hose 12 has a coiled hose portion 22, which can be circular in cross-section, on its end. The coiled hose portion 22 here is formed by a coil made of stainless steel, wherein the coil has a predetermined width, which is formed in the shape of a coil to or respectively on the hose end. The inner hose 12 can be produced as a coiled hose made of stainless steel (e.g., material 1.4305) or as a stainless steel coil.

A sleeve 20 which is wedge-shaped in the longitudinal section of FIG. 1 is arranged on the hose end of the inner hose 12 between the coiled hose portion 22, which is constant in cross-section over the length, and the protective hose 14 or respectively the braided hose 16. The sleeve 20 which is wedge-shaped in the longitudinal section is arranged with the wider end on the front-face end of the hose 11 so that the tapering contour of the wedge-shaped sleeve 20 gradually increases in diameter towards the front-end face. Because the protective hose 14 and/or the braided hose 16 abut the wedge-shaped sleeve 20, the end regions of the protective hose 14 and/or the braided hose 16 are expanded by the wedge shape of the sleeve 20.

The sleeve 20 which is wedge-shaped in longitudinal section is produced, for example, from stainless steel (e.g., material 1.4305) and has, on the end that faces the front-face end of the hose 11, a peripheral groove 24 in which the end(s) of the braided hose 16 and/or of the protective hose 14 are received.

In the region of the wedge-shaped longitudinal extension of the sleeve 20, the outer protective hose 14 is surrounded on its outer side by a sealing body 30. The sealing body 30 here acts as a counter-wedge to the wedge-shaped longitudinal extension of the sleeve 20. The sealing body 30 is configured such that is has a truncated-conical hollow space in which the end of the coiled hose portion 22 along with the sleeve 20 which is wedge-shaped in the longitudinal section and the end(s) of the braided hose 16 and/or of the outer protective hose 14 abutting the sleeve 20 are received. To prevent the sealing body from slipping in the longitudinal direction of the hose 11, a nut 32 is arranged on the outside of the hose 11.

The sealing body 30 is further configured with peripheral ribs 34 on the outside in the circumferential direction, which are brought into contact with a connector body 50. The nut 32 is produced, for example, from stainless steel (e.g., material 1.4305) and has an inner thread 36 that engages with the outer thread of the connector body 50 when the connector body 50 is introduced into the interspace formed between the sealing body 30 and the inner thread 36. When the connector body 50 is screwed in, the sealing body 30 is pressed against the end region of the protective hose 14, which region is expanded by the sleeve 20 which is wedge-shaped in the longitudinal section.

The sleeve 20 has a peripheral collar 28 on the front-face end of the hose, wherein the collar 28 is configured with an undercut 29 which faces away from the free end of the hose 11. A nose-shaped projection 42 of an end sleeve 40 arranged on the front face of the hose engages with the undercut 29.

Figure 2:
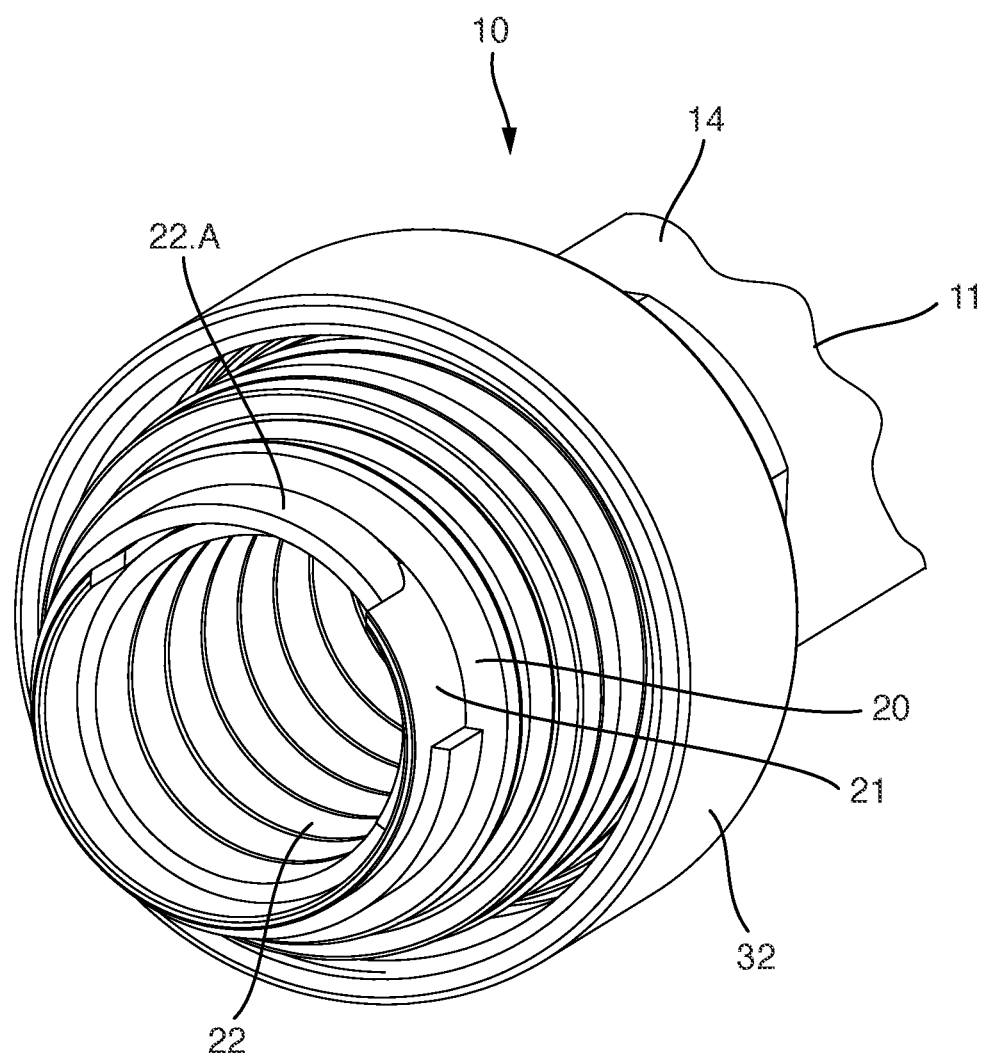
FIG. 2 schematically illustrates a perspective view of the hose connection.

Furthermore, the sleeve 20 can have circular continuation body 21 on the side facing the end sleeve 40. The continuation body 21 can be circular, i.e., configured with an opening between the two ends (cf. FIG. 2). On the front-face end that faces the end sleeve 40, the coiled hose portion 22 has a coiled end portion 22.A, which is guided through the opening in the continuation body 21 (cf. FIG. 2) and is arranged on the outside of the continuation body, such as by forming a clamping effect. Here, the radial distance of the coiled end portion 22.A to the central longitudinal axis of the coiled hose portion 22 is larger than the radial distance of the coiled hose portion 22 to the central longitudinal axis of the coiled hose portion 22 in the interior of the hose 11.

When the end sleeve 40 is arranged at the front-face end of the hose 11, the coiled end portion 22.A is arranged or clamped between the side of the sleeve 22 facing the front face of the collar 28 and the inside of the end sleeve 40. The coiled end portion 22.A in interaction with the clamping forces of the inner hose 12, the sleeve 20, and the end sleeve 40 prevents the coil or respectively the coiled end portion 22.A from rotating out.

The coupling sleeve 40 is produced from PEEK (polyether ether ketone). In another embodiment, the coupling sleeve 40 is produced from metal or another plastic. In addition, in one embodiment the molded-on sealing body 30 is produced from polytetrafluorethylene (PTFE).

The hose connection 10 is configured to be fluid-tight, wherein there is no narrow point constricting the (inner) diameter in the region of the coiled hose portion 22, so that cables, light bundles, working channels, e.g., for instruments, etc., can be easily inserted into the hose 11. The formation of a narrow point constricting the inner diameter of the coiled hose portion 22 in this region is prevented, because the coiled end portion 22.A is crimped and does not abut the wedge-shaped sleeve 20.

Figure 3:
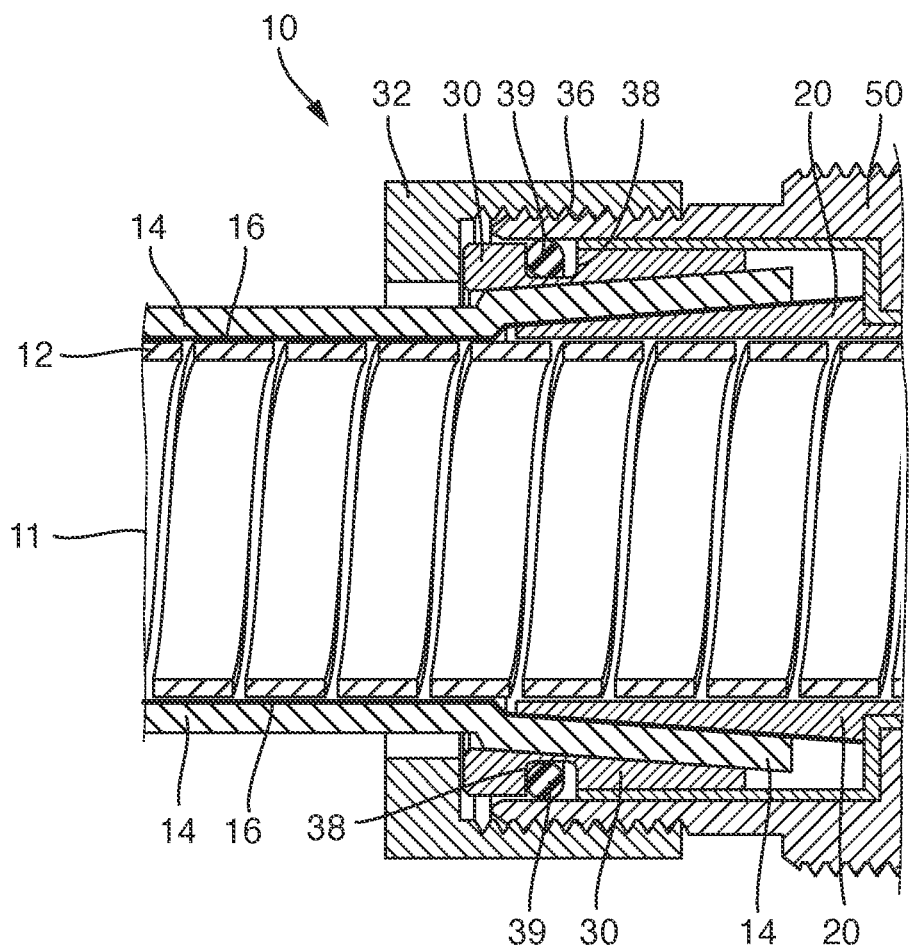
FIG. 3 schematically illustrates a cross-section through a further hose connection in detail.

FIG. 3 shows a section of a hose connection 10 according to another embodiment in cross-section. Compared to the embodiment shown in FIG. 1, the hose connection 10 has a sealing body 30 which is wedge-shaped in the longitudinal section of FIG. 3 and which is configured with a receiving groove 38 on its outside in the circumferential direction. An O-shaped sealing ring 39 is arranged in the receiving groove 38 so that the connector body 50 is sealed in relation to the sealing body 30 by the sealing ring 39 when the connector body 50 is introduced into the interspace formed between the sealing body 30 and the inner thread 36. In one embodiment, the connector body 50 can be configured in the region of the sealing ring 39 with a groove or trough formed on the inside on the side facing the sealing ring 39.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be construed to cover all modifications that may fall within the scope of the appended claims.

LIST OF REFERENCE SIGNS

10 Hose connection
11 Hose
12 Inner hose
14 Protective hose
16 Braided hose
20 Sleeve
21 Continuation body
22 Coiled hose portion
22.A Coiled end portion 24 Groove
28 Collar
29 Undercut
30 Sealing body
32 Nut
34 Rib
36 Inner thread
38 Receiving groove
39 Sealing ring
40 End sleeve
50 Connector body

What is claimed is:

1. A fluid-tight hose connection for a surgical instrument comprising:
   a hose having an inner hose and an outer protective hose surrounding the inner hose, wherein the inner hose has a coiled hose portion at an end portion of the hose;
   a sleeve having a first wedge-shape in a longitudinal section, the sleeve being arranged between the coiled hose portion of the inner hose and the outer protective hose;
   a sealing body surrounding the protective hose and arranged on an outside of the protective hose at a longitudinal position of the hose corresponding to the sleeve;
   a connector body having an internal surface forming an interspace with an outer circumferential surface of the sealing body; and
   a nut;
   wherein the sealing body having a second wedge-shape in the longitudinal section;
   the outer circumferential surface of the sealing body having at least one peripheral rib extending circumferentially around the outer circumferential surface;
   the at least one peripheral rib has a curved outer surface protruding outwardly in a radial direction from the outer circumferential surface of the sealing body to contact the internal surface of the connector body; and
   the nut is threadingly engaged with an outer surface of the connector body to maintain contact of the curved outer surface of the at least one peripheral rib with the internal surface of the connector body.

2. The fluid-tight hose connection according to claim 1, wherein the sleeve having a sleeve body with a truncated-conical outer side facing the outer protective hose and with a cylindrical hollow space at least partially receiving the coiled hose portion of the inner hose.

3. The fluid-tight hose connection according to claim 1, wherein the sleeve is arranged between the coiled hose portion of the inner hose and the protective hose such that an end of the sleeve that is wider in diameter corresponds to a free end of the hose.

4. The fluid-tight hose connection according to claim 1, wherein the hose further comprises a braided hose arranged between the coiled hose portion of the inner hose and the outer protective hose, wherein the braided hose surrounds the sleeve at the free end of the hose.

5. The fluid-tight hose connection according to claim 1, wherein the sleeve comprises a peripheral groove formed in a circumferential direction for receiving an end of the protective hose.

6. The fluid-tight hose connection according to claim 4, wherein the sleeve comprises a peripheral groove formed in a circumferential direction for receiving an end of the protective hose and an end of the braided hose.

7. The fluid-tight hose connection according to claim 1, wherein the second wedge-shape of the sealing body comprises a truncated-conical interior for receiving the end portion of the hose, the end portion surrounding the sleeve.

8. The fluid-tight hose connection according to claim 1, wherein the sealing body is arranged on the protective hose such that an end of the sealing body that is smaller in diameter corresponds to the end of the hose.

9. The fluid-tight hose connection according to claim 1, wherein the coiled hose portion of the inner hose having a coiled end portion, wherein the coiled end portion is configured as an end-side protrusion.

10. The fluid-tight hose connection according to claim 9, wherein a radial distance of the protrusion to a central longitudinal axis of the coiled hose portion is larger than a radial distance of the coiled hose portion facing away from the coiled end portion to a central longitudinal axis of the coiled hose portion.

11. The fluid-tight hose connection according to claim 9, wherein the coiled end portion is one of:
   arranged between the sleeve and an end sleeve arranged on a front-face end of the hose; and
   arranged to surround an outside of a continuation body which extends to the front-face end of the hose.

12. The fluid-tight hose connection according to claim 1, further comprising a collar having an undercut facing the end of the hose and extending circumferentially around the sleeve.

13. The fluid-tight hose connection according to claim 12, wherein the collar having a latching contour for latching a latching projection of a front-face end sleeve.

14. The fluid-tight hose connection according to claim 1, further comprising an outer cuff surrounding the end portion of the hose.

15. A surgical instrument comprising the fluid-tight hose connection according to claim 1.

16. The fluid-tight hose connection according to claim 1, wherein the at least one peripheral rib is integrally formed with the sealing body.

17. A fluid-tight hose connection for a surgical instrument comprising:
   a hose having an inner hose and an outer protective hose surrounding the inner hose, wherein the inner hose has a coiled hose portion at an end portion of the hose;
   a sleeve having a first wedge-shape in a longitudinal section, the sleeve being arranged between the coiled hose portion of the inner hose and the outer protective hose;
   a sealing body surrounding the protective hose and arranged on an outside of the protective hose at a longitudinal position of the hose corresponding to the sleeve;
   a connector body having an internal surface forming an interspace with an outer circumferential surface of the sealing body; and
   a nut;
   wherein the sealing body having a second wedge-shape in the longitudinal section;
   the outer circumferential surface of the sealing body having a receiving groove extending circumferentially around the outer circumferential surface for receiving a seal;
   the seal has a curved outer surface protruding outwardly in a radial direction from the outer circumferential surface of the sealing body to contact the internal surface of the connector body; and the nut is threadingly engaged with an outer surface of the connector body to maintain contact of the curved outer surface of the seal with the internal surface of the connector body.

* * * * *